(12) United States Patent
Brenneman et al.

(10) Patent No.: US 8,226,592 B2
(45) Date of Patent: Jul. 24, 2012

(54) METHOD OF TREATING COPD WITH ARTIFICIAL ARTERIO-VENOUS FISTULA AND FLOW MEDIATING SYSTEMS

(75) Inventors: Rodney A. Brenneman, San Clemente, CA (US); J. Christopher Flaherty, San Clemente, CA (US)

(73) Assignee: ROX Medical, Inc., San Clemente, CA (US)

( * ) Notice: Subject to any disclaimer, the term of this patent is extended or adjusted under 35 U.S.C. 154(b) by 216 days.

(21) Appl. No.: 11/013,981

(22) Filed: Dec. 15, 2004

(65) Prior Publication Data

US 2006/0129083 A1     Jun. 15, 2006

(51) Int. Cl.
*A61M 5/00*     (2006.01)

(52) U.S. Cl. .............. 604/9; 604/6.16; 604/7; 604/8; 604/10; 604/65; 604/66; 604/67; 604/264; 606/153; 606/157; 606/158; 623/1.1; 623/1.13; 623/1.24; 623/1.25

(58) Field of Classification Search .............. 604/6.16, 604/7–10, 65–67, 264; 606/153, 157, 158; 623/1.1, 1.13, 1.25
See application file for complete search history.

(56) References Cited

U.S. PATENT DOCUMENTS

| | | | | |
|---|---|---|---|---|
| 3,538,917 A | * | 11/1970 | Selker | 606/158 |
| 3,675,656 A | * | 7/1972 | Hakim | 606/158 |
| 3,730,186 A | * | 5/1973 | Edmunds et al. | 606/158 |
| 3,882,862 A | | 5/1975 | Berend | |
| 4,586,501 A | * | 5/1986 | Claracq | 606/158 |
| 4,601,718 A | * | 7/1986 | Possis et al. | 623/1.26 |
| 4,828,544 A | * | 5/1989 | Lane et al. | 604/9 |
| 5,108,420 A | | 4/1992 | Marks | |
| 5,258,042 A | | 11/1993 | Mehta | |
| 5,491,224 A | | 2/1996 | Bittner et al. | |
| 5,507,725 A | | 4/1996 | Savage et al. | |
| 5,756,696 A | | 5/1998 | Gray et al. | |
| 5,830,222 A | | 11/1998 | Makower | |
| 5,830,224 A | | 11/1998 | Cohn et al. | |
| 5,843,170 A | | 12/1998 | Ahn | |
| 6,053,891 A | * | 4/2000 | DeCampli | 604/288.01 |
| 6,099,542 A | | 8/2000 | Cohn et al. | |
| 6,120,534 A | * | 9/2000 | Ruiz | 623/1.19 |
| 6,152,937 A | | 11/2000 | Peterson et al. | |
| 6,168,620 B1 | | 1/2001 | Kerr | |
| 6,174,681 B1 | | 1/2001 | Halling et al. | |

(Continued)

FOREIGN PATENT DOCUMENTS

EP        1614400 A2     1/2006

(Continued)

OTHER PUBLICATIONS http://www.emedicinehealth.com/causes_of_erectile_dysfunction/page3_em.htm.*

(Continued)

*Primary Examiner* — Tatyana Zalukaeva
*Assistant Examiner* — Ginger T Chapman
(74) *Attorney, Agent, or Firm* — Levine Bagade Han LLP

(57) ABSTRACT

A method for treatment of COPD, hypertension, and left ventricular hypertrophy, and chronic hypoxia including creation of an artificial arterio-venous fistula and installation of a flow mediating device proximate the fistula. The flow mediating device is operated to limit flow as medically indicated to provide the optimum amount of bypass flow.

27 Claims, 5 Drawing Sheets

U.S. PATENT DOCUMENTS

| | | |
|---|---|---|
| 6,376,188 B1 | 4/2002 | Halling et al. |
| 6,391,036 B1 | 5/2002 | Berg et al. |
| 6,451,048 B1 | 9/2002 | Berg et al. |
| 6,579,311 B1 | 6/2003 | Makower |
| 6,616,675 B1 | 9/2003 | Evard et al. |
| 6,669,709 B1 | 12/2003 | Cohn et al. |
| 6,695,878 B2 | 2/2004 | McGuckin, Jr. et al. |
| 6,746,426 B1 | 6/2004 | Flaherty et al. |
| 6,746,464 B1 | 6/2004 | Makower |
| 6,926,690 B2 | 8/2005 | Renati |
| 6,979,351 B2 * | 12/2005 | Forsell et al. .................. 623/3.1 |
| 6,985,774 B2 * | 1/2006 | Kieval et al. .................... 607/44 |
| 7,011,094 B2 | 3/2006 | Rapacki et al. |
| 7,056,326 B2 | 6/2006 | Bolduc et al. |
| 7,316,706 B2 | 1/2008 | Bloom et al. |
| 7,628,768 B2 * | 12/2009 | Faul et al. ......................... 604/8 |
| 7,967,769 B2 * | 6/2011 | Faul et al. ......................... 604/8 |
| 2002/0189727 A1 | 12/2002 | Peterson |
| 2003/0088256 A1 | 5/2003 | Conston et al. |
| 2003/0100920 A1 | 5/2003 | Akin et al. |
| 2004/0087997 A1 | 5/2004 | Brenneman |
| 2004/0249334 A1 * | 12/2004 | Cull ................................. 604/9 |
| 2004/0249335 A1 * | 12/2004 | Faul et al. ......................... 604/9 |
| 2005/0049675 A1 | 3/2005 | Wallace |
| 2005/0107733 A1 | 5/2005 | Faul et al. |
| 2005/0124892 A1 | 6/2005 | Weitzel et al. |
| 2005/0228402 A1 | 10/2005 | Hofmann |
| 2006/0047337 A1 | 3/2006 | Brenneman |
| 2006/0129083 A1 | 6/2006 | Brenneman et al. |
| 2006/0206123 A1 | 9/2006 | Brenneman |
| 2006/0293701 A1 | 12/2006 | Ainsworth et al. |

FOREIGN PATENT DOCUMENTS

| | | |
|---|---|---|
| WO | WO 01/05463 | 1/2001 |
| WO | WO 2006/026279 A2 | 3/2006 |
| WO | WO 2006/066210 A2 | 6/2006 |
| WO | WO 2007/005386 A1 | 1/2007 |
| WO | WO 2007/014283 A2 | 2/2007 |

OTHER PUBLICATIONS

"Chronic Obstructive Pulmonary Disease (COPD) Fact Sheet (Chronic Bronchitis and Emphysema)", Feb. 16, 2007, American Lung Association website, www.lungusa.org/site/pp.asp?e=dvLUK9OOE&b=35020.

"COPD: How is COPD Treated?", Feb. 16, 2007, National Heart Lung and Blood Institute Diseases and ConditionS Index website, www.nhlbi.nih.gov/health/dci/Diseases/Copd/Copd_Treatments.html.

"Lung—Treatment of COPD and Asthma", Feb. 16, 2007, NLHPE website, www.nlhep.org/lung.trtmnt.html.

Ruebben, et al., "Arteriovenous fistulas induced by femoral arterial catheterization: percuntaneous treatment," *Radiology*, 209:729, 1998.

Schlensak, et al., "Pulmonary Artery Banding with a Novel Percuntaneously, Bidirectionally Adjustable Device," *Eur. J. of Cardio-thoracic Surg.*, pp. 931-933, 1997.

* cited by examiner

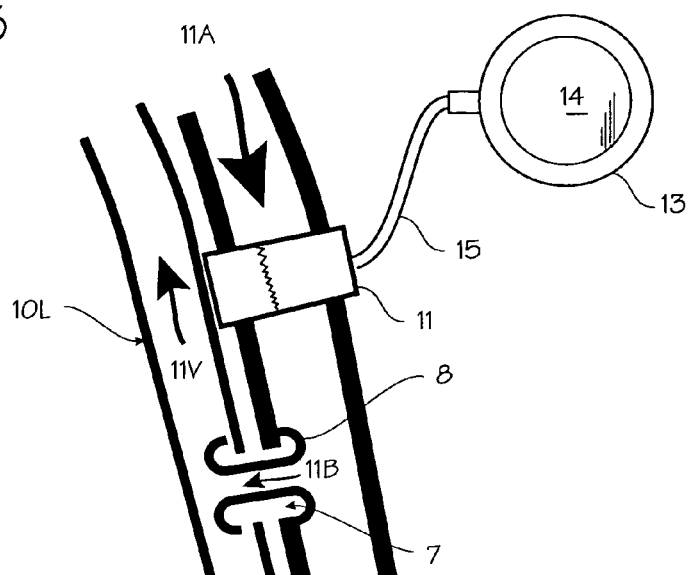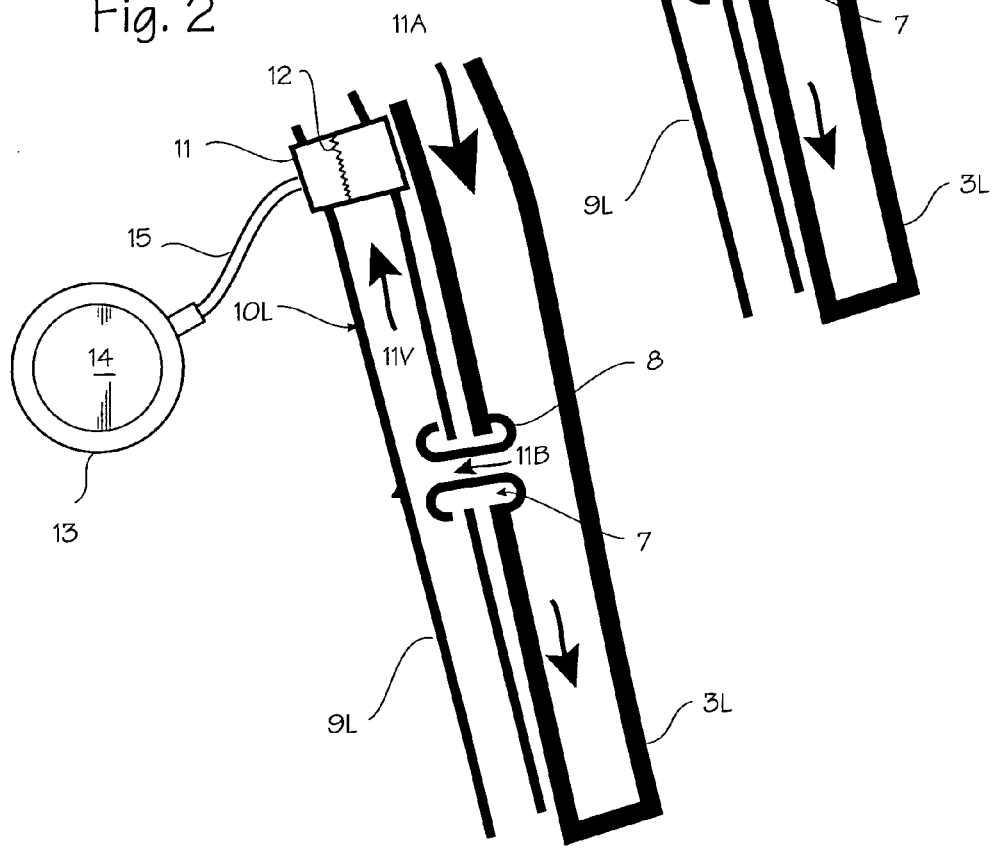

METHOD OF TREATING COPD WITH ARTIFICIAL ARTERIO-VENOUS FISTULA AND FLOW MEDIATING SYSTEMS

FIELD OF THE INVENTIONS

The inventions described below relate to treatments for pulmonary hypertension and vascular surgery.

BACKGROUND OF THE INVENTIONS

Chronic obstructive pulmonary disease (COPD), chronic hypoxia, hypertension, and left ventricular hypertrophy and pulmonary hypertension are diseases of the cardiopulmonary system. Chronic obstructive pulmonary disease (COPD), which includes chronic bronchitis and emphysema, is a slowly progressive lung disease caused primarily by smoking. In COPD, the lungs are damaged and the airways are partly obstructed, making it difficult to breath and leading to a gradual loss of lung function. Symptoms of COPD include chronic cough, excessive sputum production, low blood oxygen levels and severe disabling shortness of breath. COPD represents the fourth leading cause of death in the United States. Chronic hypoxia (reduction of oxygen supply to the body despite adequate blood flow through the body), hypertension, and left ventricular hypertrophy are related conditions which may be symptomatic of COPD or coincident with COPD.

These serious conditions affect many people, and the primary treatments are merely ameliorative. The primary treatments for COPD include avoidance of irritants such as tobacco smoke and breathing supplemental oxygen. In advanced cases of COPD, lung reduction surgery is sometimes performed, but it is not clear that it helps. There is no known cure for COPD.

An aortocaval fistula (ACF) is a rare clinical condition that can be either spontaneous (80% of the cases), related to abdominal aortic aneurysm, or the result of some trauma such as lumbar disk surgery. It is currently seen as a defect that should be cured with surgery and, possibly, stent-graft implantation in the aorta. Likewise, arterio-venous fistulas are uncommon, and can be caused by trauma or may be iatrogenic (i.e., an unintended result of vascular intervention, as discussed in Ruebben, et al., *Arteriovenous fistulas induced by femoral arterial catheterization: percutaneous treatment*, 209 Radiology, 729 (1998)). Arteriovenous fistulas are also see as defects that should be cured with surgery and, possibly, stent-graft implantation.

Contrary to this understanding, an intentionally formed aortocaval fistula appears to be a viable treatment for COPD. Recently, in our co-pending U.S. patent application Ser. No. 10/820,169 filed Apr. 6, 2004, entitled *Implantable Arteriovenous Shunt Device* and listing John L. Faul, Toshihiko Nishimura, Peter N. Kao & Ronald G. Pearl as inventors (the entirety of which is hereby incorporated by reference), we propose creation of an artificial aortocaval fistula as a treatment for COPD, and we disclose the method of creating the fistula and an implantable shunt for maintaining the aortocaval fistula. In our co-pending U.S. patent application Ser. No. 10/927,704 filed Aug. 27, 2004 (the entirety of which is hereby incorporated by reference) we disclose a vascular shunt rivet which serves to hold contiguous points of the patient's aorta and inferior vena cava (or other arteries and their associated veins, such as the femoral artery and femoral vein, or the carotid artery and the carotid vein) together and maintain an open flow path from the aorta to the vena cava. The device functions as a rivet, holding the two vessel walls in close proximity, and as a shunt, permitting and maintaining flow from one blood vessel to the other as a treatment for COPD.

The method of treating COPD by creating an artificial arterio-venous fistula and maintaining the fistula with an endoprosthesis may be improved with the addition of mechanisms for adjusting the arterial bypass flow rate to optimum levels. Adjustments to flow may be made to balance the positive effects of injecting oxygenated blood into the venous system with the potential negative effects.

SUMMARY

The devices and methods described below provide for treatment of COPD, hypertension, and left ventricular hypertrophy, and chronic hypoxia. After creation of an artificial arterio-venous fistula, a flow mediating device is installed proximate the fistula (directly on the fistula, immediately upstream of the fistula in the artery, or immediately downstream of the fistula in the vein). In one embodiment of the method, a bladder is installed proximate the vein, artery or the fistula itself, and is inflated to impinge upon the vein, artery or the fistula to limit bypass flow through the fistula. Other mechanisms for controlling flow are also proposed, including shunts (placed to maintain the fistula) having mechanisms for throttling flow through the shunt, and even prior art screw operated clamps for compressing some portion of the flow path.

BRIEF DESCRIPTION OF THE DRAWINGS

FIG. 2 is a detail view of the inflatable cuff and its associated components, installed over the femoral vein of the patient.

FIG. 3 illustrates installation of the cuff over the left femoral artery.

DETAILED DESCRIPTION OF THE INVENTIONS

Figure 1:
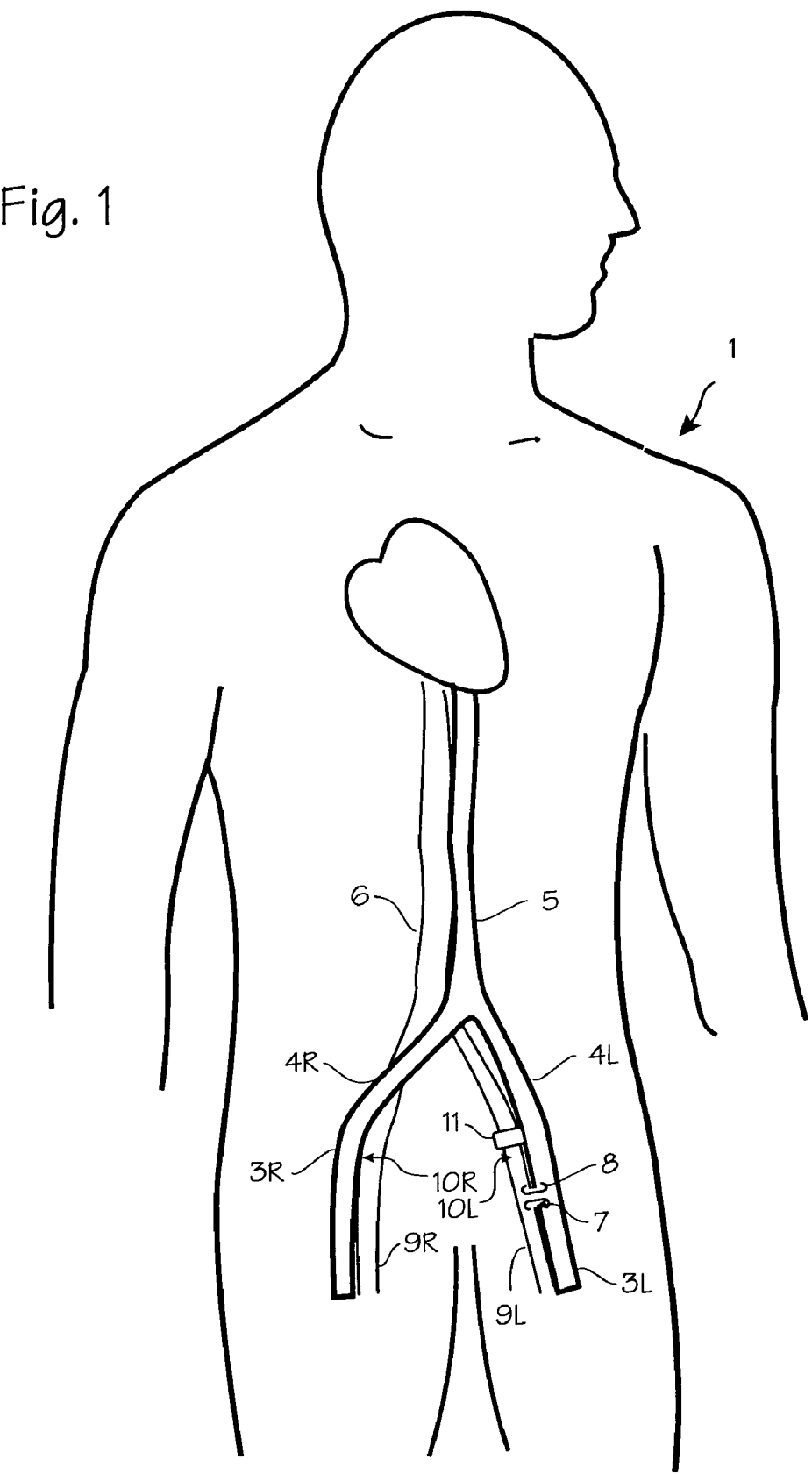
FIG. 1 illustrates the method of creating an artificial arterio-venous fistula and controlling flow with a balloon impinging on the artery.

FIG. 1 illustrates the method of creating an artificial arterio-venous fistula and controlling flow with a balloon impinging on the artery. A portion of the vasculature of the patient 1 is shown, illustrating the left and right femoral artery/external femoral arteries 3L and 3R, the left and right common iliac arteries 4L and 4R, and the abdominal aorta 5. Portions of the venous system are also illustrated the vena cava 6, which runs parallel to the aorta, and is typically contiguous with the aorta, the left and right femoral veins 9L and 9R. An artificial arterio-venous fistula or side-to-side anastomosis 7 may be formed between the femoral vein and femoral artery on either side of the body, indicated as items 10R and 10L, or between the iliac artery and the femoral vein, and at locations within the aorta, as indicated at item 7. The artificial fistula may be maintained as an anatomical fistula, consisting of vascular tissue, if the local anatomy tends to heal to a stable and patent fistula, or it may be maintained by shunt or shunt rivet 8 as illustrated, or by an endoprosthesis (a vascular graft or stent graft) of significant length.

To regulate flow through the fistula, an inflatable cuff 11 is placed and implanted around the femoral vein, proximal to the fistula (closer to the heart relative to the fistula). The inflatable cuff is further illustrated in FIG. 2, which shows the inflatable cuff assembly which includes the cuff 11, secured around the vein with suture seam 12, a subcutaneous injection port 13 with a resealable membrane 14, and a short conduit 15 providing for fluid communication between the injection port and the cuff (the injection port and resealable membrane may also be formed integrally with the cuff). The cuff may also be installed over the femoral artery 3L, proximal to the fistula, as shown in FIG. 3. Inflation of the cuff results squeezing the blood vessel within the cuff, essentially throttling flow through the blood vessel. The degree to which flow is mediated or throttled depends on the degree to which the cuff is inflated.

Figure 4:
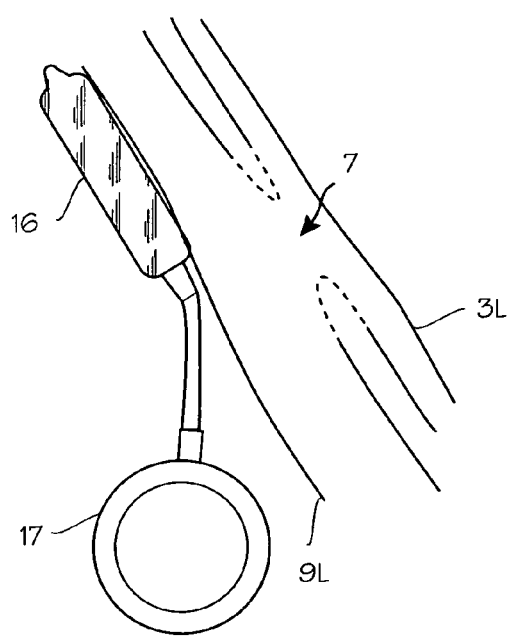
FIGS. 4, 5 and 6 illustrate use of bladder which merely impinges on the femoral vein to control bypass flow.
Figure 5:
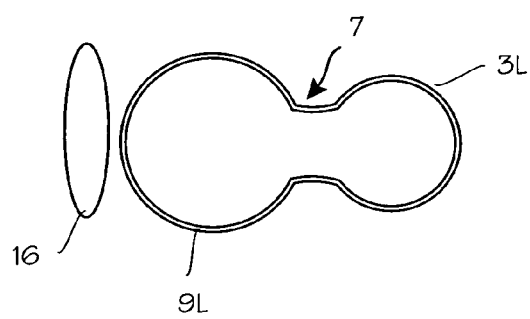
Figure 6:
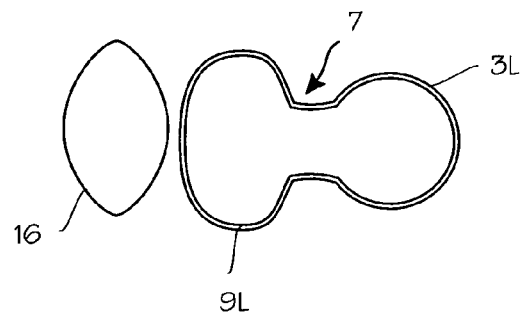

FIGS. 4, 5 and 6 illustrate use of bladder which merely impinges on the femoral vein to control bypass flow. As shown in FIG. 4, a bladder is placed in immediate contact with the femoral vein 9. The fistula 7 is shown in phantom, and may be fitted with a shunt or rivet 8. The bladder 16 is an elongate bladder, which may be conformal or non-conformal, which is inflated through the associated access port 17. FIG. 5 shows a cross section of the leg, with the bladder uninflated, impinging on the femoral vein, while FIG. 6 illustrates the effect of the inflated bladder on the femoral vein. Upon inflation, the bladder further impinges upon the femoral vein to impede flow, and thereby impede bypass flow from the femoral artery to the femoral vein.

Figure 9:
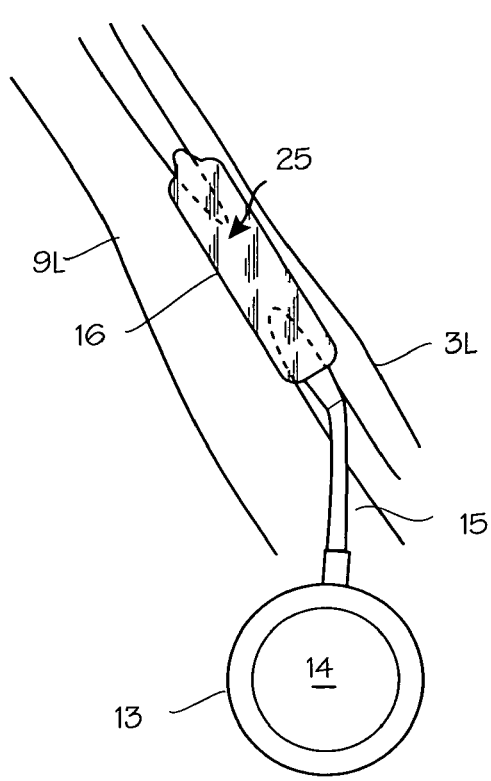
FIG. 9 shows the bladder assembly of FIG. 8 disposed in impinging relationship with the anatomical fistula.
Figure 8:
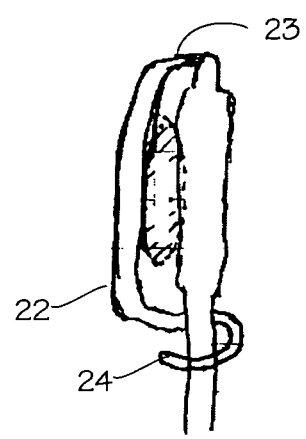
FIGS. 7 and 8 illustrate a bladder assembly which assists in operably coupling the bladder to the blood vessel.
Figure 7:
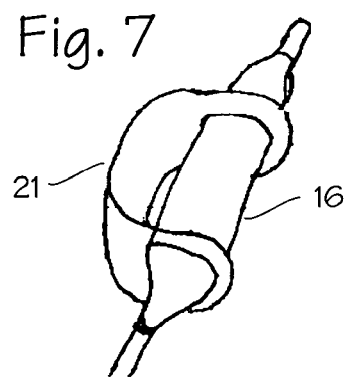

FIGS. 7 and 8 illustrate a bladder assembly which assists in operably coupling the bladder to the blood vessel, so that distention of the bladder is certain to result in impingement on the blood vessel. In FIG. 7, the bladder 16 is coupled to a band 21 which provides an anvil against which the balloon pushes the blood vessel, and prevents the blood vessel from merely moving in response to balder inflation. The band may be attached to the balloon at each end, as shown, or the band may be wrapped completely around both the bladder and the blood vessel. FIG. 8 illustrates another a bladder assembly which assists in operably coupling the bladder 16 to the blood vessel, so that distention of the bladder is certain to result in impingement on the blood vessel. In this figure, a relatively hard and rigid clip 22 is hinged or otherwise rotatably attached to the balloon at hinge point 23, on one end or the other, and is fastened with the hook or other closure mechanism 24 at the other, so that the bladder may be fastened to the blood vessel. The clip is narrow and elongate, so that it may be used as shown in FIG. 9, with the bladder 16 disposed in impinging relationship with the anatomical fistula 25 and the clip disposed on the opposite side of the fistula and closed upon the bladder or an extending structure (in this case, the conduit used to fill the bladder). If a graft of significant length is used, the devices of FIGS. 7, 8 and 9 may be placed over contiguous parallel segments of the shunt and artery, or the shunt and the vein.

Any other adjustable vascular impingement device may be used, including the Flow-watch® pulmonary artery band system which includes a jack screw adjusted by a motor which is powered and controlled telemetrically, as described in Stergiopulis, *Flow Control Device and Method*, PCT App. PCT/EP00/06907 (Jan. 25, 2001), or screw operated bands such as those disclosed in Schlensak, et al., *Pulmonary Artery Banding With A Novel Percutaneously, Bidirectionally Adjustable Device,* 12 Eur. J. of Cardio-thoracic Surg. 931-933 (1997).

The devices and methods described above may be used to treat COPD as follows. First, a surgeon creates a fistula between an artery and a nearby vein. Preferably, the artery and vein are large, such as the femoral artery and the femoral artery. The fistula may be maintained, after artificial creation, either naturally to create an anatomical fistula comprising portions of the contiguous artery and vein healed together, or it may be a mechanically maintained fistula which is supported with a shunt or stent, or it may comprise a distinct shunt from the artery to the vein. After creating and stabilizing the fistula (ensuring that endoprosthesis are securely implanted, or that the anatomical fistula is structurally sound), the surgeon implants the flow restricting device (which may be any one of the devices described or mentioned herein) around the vein downstream from the fistula, or around the artery upstream from the fistula, or across the fistula itself. To control flow through the fistula, the cuff is inflated or deflated as necessary to achieve a desired bypass flow volume. The desired by-pass flow volume is determined by monitoring blood oxygenation and cardiac function intraoperatively (that is, immediately after creation of the fistula and implantation of the flow restricting device) and/or (that is, before discharge) and adjusting bypass flow to obtain a medically indicated short-term change in such parameters. The desired by-pass flow should also be determined and adjusted post-operatively, after a stabilization period (a few weeks after surgery). The shunt will increase mixed venous oxygenation, (SvO2), increase the percentage of oxygen bound to hemoglobin (SpO2), increase the amount of oxygen dissolved in blood plasma (PaO2), and increase cardiac output and stroke volume (after remodeling). Initially (immediately after opening the shunt) the heart rate increases to provide increased cardiac output. Then, as the heart 'remodels' the stroke volume increases and the heart rate comes back down to normal levels to maintain increased cardiac output. Lower bypass flow in the post-operative and stabilization time period may be desirable to avoid over stressing the heart and allow a more gradual cardiac re-modeling. Thus, the overall procedure may be accomplished by adjusting flow in the peri-operative and stabilization time frame to levels sufficient to increase $PaO_2$ and/or $SvO_2$ about 5% or more, and increase cardiac output by about 10% or more, followed by re-evaluation of the patient after stabilization and readjustment of by-pass flow to provide for an increase $PaO_2$ and/or $SvO_2$ (relative to pre-operative levels) of about 10% to 20% or more, depending on patient tolerance. Should the heart rate increase attendant to the bypass flow be more tolerable, the bypass flow in the peri-operative and stabilization time frame may adjusted to higher levels, to provide for an increase in $PaO_2$ and/or $SvO_2$ of about 20% to 25% (for a COPD with low $PaO_2$ and/or $SvO_2$), followed by re-evaluation of the patient after stabilization (after long-term remodeling of the heart, the heart may be remodeled in response to the therapy) and reduction of by-pass flow to provide for an increase $PaO_2$ and/or $SvO_2$ (relative to pre-operative levels) by about 10% to 20%. The optimal levels of these parameters, and the optimum trade-off between increased blood levels, cardiac output and increased heart rate are expected to be refined with clinical experience.

Figure 10:
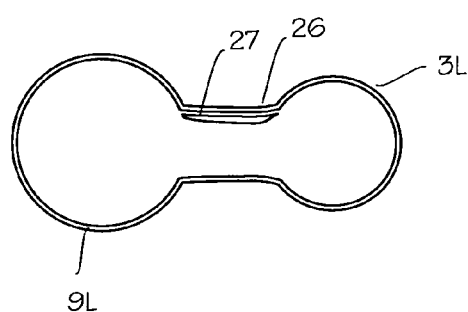
FIGS. 10 and 11 illustrate use of shunt with an integral bladder, which may be inflated to control flow through the shunt, as desired to affect the arterial bypass flow as treatment for COPD.
Figure 11:
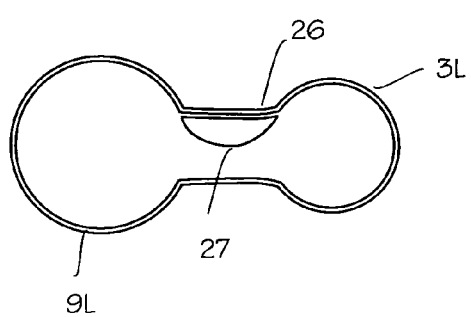

Rather than impinging on the blood vessel as described above, the desired flow control may be achieved by providing a shunt with a variable lumen cross-section or other flow control means which may act as a throttle valve. FIGS. 10 and 11 illustrate use of shunt with an integral bladder which may be inflated to control flow through the shunt, as desired to effect the arterial bypass flow as treatment for COPD. A shunt 26 is installed between the femoral artery and the femoral vein. The shunt additionally comprises a bladder 27 installed within the lumen of the shunt, which is filled as desired through the inflation port 28. As illustrated in FIG. 11, in which the bladder is partially inflated, the bladder partially occludes the shunt, to a degree dependent on the degree to which the bladder is inflated. The bladder may be fully inflated to fully occlude the shunt and prevent bypass flow. The shunt may be made of any suitable shunt material.

Figure 12:
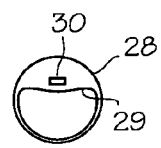
FIGS. 12 and 13 illustrate another mechanism for regulating fistula bypass flow, in which a membranous wall of the shunt may be magnetically drawn to control the size of the shunt lumen.
Figure 13:
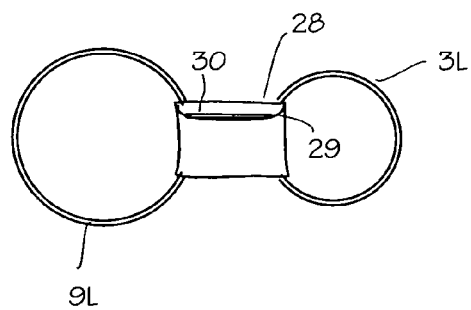

FIGS. 12 and 13 illustrate another mechanism for regulating fistula bypass flow, in which a membranous wall of the shunt may be magnetically drawn to control the size of the shunt lumen. In this embodiment, the shunt is provided with an rigid outer wall 29 and flexible inner wall 30. The dissectible portion of the inner wall which cuts across the lumen may be elastic or merely loose, so that it may be pulled against the outer wall to fully open the lumen. A magnet (or ferromagnetic mass) 31 is fixed to the dissectible portion of the inner wall, such that the magnet, and thus the dissectible portion of the inner wall, may be drawn against the outer by magnetic attraction to an extracorporeal magnet 32. The extracorporeal magnet may be an electromagnet with operating circuitry which is fixed to the patient in proximity to the shunt, or it may be a permanent magnet, the power of which may be selected to effect a desired degree of openness.

While the devices and methods have been described relative to the femoral artery and femoral vein, they may also be employed in other suitable contiguous or associated artery/vein pairs, including the aorta and inferior vena cava, the femoral vein and the iliopopliteal vein or iliac vein, the popliteal artery and popliteal vein, the carotid artery and the jugular vein, the brachial artery and brachial vein, the brachial artery and brachial vein, and the brachio-cephallic artery and subclavian vein. The artery-to-vein shunt may also be provided between remote anastomosis cites, such as the iliac artery to the inferior vena cava. Also, though discussed in terms of COPD treatment, the method should be useful to treat hypertension (pulmonary hypertension and arterial hypertension), left ventricular hypertrophy, and chronic hypoxia. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of treating COPD in a patient, said method comprising the steps of:
   identifying symptoms of COPD;
   creating an artificial fistula via a shunt between an artery and a vein of the patient such that blood flows through the shunt between the artery and vein;
   installing a flow mediating device separate from the fistula and the shunt and in contact against the artery or vein such that substantial blood flow through the fistula between the artery and vein is maintained when the flow mediating device is in use; and
   operating the flow mediating device along the artery or vein throttling flow through the blood vessel to restrict bypass blood flow through the fistula as indicated to treat COPD.

2. The method of claim 1 further comprising:
   operating the flow-mediating device to control bypass blood flow through the fistula to achieve an increase in the patient's $PaO_2$ by at least about 5% as indicated to treat COPD.

3. The method of claim 1 further comprising:
   operating the flow-mediating device to control bypass blood flow through the fistula to achieve an increase in the patient's $SvO_2$ by at least about 5% as indicated to treat COPD.

4. The method of claim 1 further comprising:
   operating the flow-mediating device to control bypass blood flow through the fistula to achieve an increase in the patient's cardiac output by at least about 10% as indicated to treat COPD.

5. The method of claim 1 further comprising:
   evaluating the patient after a stabilization period and adjusting the flow mediating device to control bypass blood flow through the fistula to achieve an increase in the patient's cardiac output by at least about 10%.

6. The method of claim 1 further comprising:
   providing the flow control device in the form of an inflatable bladder system comprising an inflatable cuff adapted to substantially surround a portion of the patient's vasculature proximate the fistula and means for delivering fluid to the inflatable cuff.

7. The method of claim 1 further comprising:
   providing the flow control device in the form of an inflatable bladder adapted to impinge upon a portion of the patient's vasculature proximate the fistula and means for delivering fluid to the inflatable bladder.

8. The method of claim 1 further comprising the steps:
   of providing a band adapted to surround a vessel of the patients vasculature and securing the bladder to the patients vasculature with the band, proximate the fistula.

9. The method of claim 1 further comprising:
   providing the flow control device in the form of an inflatable bladder adapted to impinge upon a portion of the patient's vasculature proximate the fistula, rigid fastener operably connected to the bladder and means for delivering fluid to the inflatable bladder; and
   installing the bladder against a portion of the patient's vasculature proximate the fistula and securing the bladder against the portion of the patient's vasculature by placing a portion of the rigid fastener opposite the bladder with the portion of the patient's vasculature disposed between the bladder and the clip, and securing the rigid fastener to the bladder.

10. The method of claim 1 further comprising:
    providing the flow mediating device in the form of a shunt or graft having a lumen and a bladder disposed within the lumen, and inflating the bladder as desired to occlude the lumen to the degree necessary to obtain desired bypass flow.

11. The method of claim 1 further comprising:
    providing the flow mediating device in the form of a shunt or graft having a lumen and a dissectible wall portion within the lumen, a magnetic mass fixed to the dissectible wall portion, said magnetic mass being operable to deflect the dissectible wall portion when acted upon by a magnet.

12. The method of claim 1 further comprising:
    squeezing or releasing the flow mediating device as desired to mediate flow through the shunt or graft.

13. The method of claim 1 further comprising:
    placing the flow mediating device on the vein downstream from the fistula.

14. The method of claim 1 further comprising:
placing the flow mediating device on the artery upstream from the fistula.

15. The method of claim 1 further comprising:
creating the artificial fistula between a femoral artery and femoral vein of the patient.

16. The method of claim 1 further comprising:
creating the artificial fistula between one of the following vein/artery pairs:
the aorta and inferior vena cava, the femoral vein and the iliopopliteal vein or iliac vein, the carotid artery and the carotid vein or jugular vein, the brachial artery and brachial vein, and the brachio-cephallic artery and subclavian vein.

17. The method of claim 1 wherein operating the flow mediating device comprises decreasing the bypass blood flow such that conditions adverse to the patient are avoided.

18. The method of claim 17 wherein adverse conditions comprise an increased heart rate, stress on the heart, or adverse cardiac remodeling.

19. The method of claim 1 wherein operating the flow mediating device comprises increasing the bypass blood flow such that cardiac output is increased.

20. A method of treating COPD in a patient, said method comprising the steps of:
identifying symptoms of COPD;
creating an artificial fistula via a shunt between an artery and a vein of the patient such that blood flows through the shunt between the artery and vein;
installing a flow mediating device separate from the fistula and the shunt and in contact against the artery such that blood flow through the fistula between the artery and vein is maintained when the flow mediating device is in use; and
moderating bypass blood flow through the fistula as indicated to treat COPD by restricting blood flow through the artery via the flow mediating device.

21. The method of claim 20 further comprising:
operating the flow-mediating device to control bypass blood flow through the fistula to achieve an increase in the patient's $PaO_2$ by at least about 5% as indicated to treat COPD.

22. The method of claim 20 further comprising:
operating the flow-mediating device to control bypass blood flow through the fistula to achieve an increase in the patient's $SvO_2$ by at least about 5% as indicated to treat COPD.

23. The method of claim 20 further comprising:
operating the flow-mediating device to control bypass blood flow through the fistula to achieve an increase in the patient's cardiac output by at least about 10% as indicated to treat COPD.

24. The method of claim 20 further comprising:
evaluating the patient after a stabilization period and adjusting the flow mediating device to control bypass blood flow through the fistula to achieve an increase in the patient's cardiac output by at least about 10%.

25. The method of claim 20 wherein operating the flow mediating device comprises decreasing the bypass blood flow such that conditions adverse to the patient are avoided.

26. The method of claim 25 wherein adverse conditions comprise an increased heart rate, stress on the heart, or adverse cardiac remodeling.

27. The method of claim 20 wherein operating the flow mediating device comprises increasing the bypass blood flow such that cardiac output is increased.

* * * * *